(12) United States Patent
Hoffmann et al.

(10) Patent No.: US 10,272,118 B2
(45) Date of Patent: Apr. 30, 2019

(54) COMPOSITIONS AND METHODS FOR TREATING AND REPAIRING TENDONS

(71) Applicant: REPLICEL LIFE SCIENCES INC., Vancouver (CA)

(72) Inventors: Rolf Hoffmann, Freiburg (DE); Kevin John McElwee, Vancouver (CA)

(73) Assignee: RepliCel Life Sciences Inc., Vancouver (CA)

( * ) Notice: Subject to any disclaimer, the term of this patent is extended or adjusted under 35 U.S.C. 154(b) by 326 days.

(21) Appl. No.: 14/767,577

(22) PCT Filed: Feb. 12, 2014

(86) PCT No.: PCT/US2014/016109
§ 371 (c)(1),
(2) Date: Aug. 12, 2015

(87) PCT Pub. No.: WO2014/127047
PCT Pub. Date: Aug. 21, 2014

(65) Prior Publication Data
US 2015/0374757 A1 Dec. 31, 2015

Related U.S. Application Data

(60) Provisional application No. 61/763,908, filed on Feb. 12, 2013.

(51) Int. Cl.
*A61K 35/36* (2015.01)
*C12N 5/071* (2010.01)
(Continued)

(52) U.S. Cl.
CPC .............. *A61K 35/36* (2013.01); *A61K 38/18* (2013.01); *A61K 38/1808* (2013.01);
(Continued)

(58) Field of Classification Search
None
See application file for complete search history.

(56) References Cited

U.S. PATENT DOCUMENTS

| 5,556,783 A | 9/1996 | Lavker et al. |
| 5,736,372 A | 4/1998 | Vacanti |

(Continued)

FOREIGN PATENT DOCUMENTS

| DE | 10056465 | 7/2002 |
| EP | 0980270 | 12/2003 |

(Continued)

OTHER PUBLICATIONS

Kevin J. McElwee, Sabine Kissling, Elke Wenzel, Andrea Huth, and Rolf Hoffmann, Cultured Peribulbar Dermal Sheath Cells Can Induce Hair Follicle Development and Contribute to the Dermal Sheath and Dermal Papilla, 2003, J. Invest. Dermatol., vol. 121, pp. 1267-1275.*

(Continued)

*Primary Examiner* — Renee Claytor
*Assistant Examiner* — Trent R Clarke
(74) *Attorney, Agent, or Firm* — BioMed IP

(57) ABSTRACT

The present invention relates to compositions and methods utilizing hair follicle derived Non-Bulbar Dermal Sheath cells for use in the treatment or prevention of the tendon injuries.

17 Claims, 4 Drawing Sheets

(51) Int. Cl.
| | |
|---|---|
| *C12N 5/077* | (2010.01) |
| *C12N 5/0775* | (2010.01) |
| *A61K 38/18* | (2006.01) |
| *A61K 38/19* | (2006.01) |
| *A61K 38/20* | (2006.01) |
| *A61K 38/30* | (2006.01) |
| *A61K 45/06* | (2006.01) |

(52) U.S. Cl.
CPC ...... *A61K 38/1825* (2013.01); *A61K 38/1833* (2013.01); *A61K 38/1841* (2013.01); *A61K 38/1858* (2013.01); *A61K 38/193* (2013.01); *A61K 38/204* (2013.01); *A61K 38/30* (2013.01); *A61K 45/06* (2013.01); *C12N 5/066* (2013.01); *C12N 5/0628* (2013.01); *C12N 5/0666* (2013.01); *C12N 2501/113* (2013.01); *C12N 2501/905* (2013.01)

(56) References Cited

U.S. PATENT DOCUMENTS

| | | | |
|---|---|---|---|
| 5,750,657 | A | 5/1998 | Edwardson et al. |
| 5,759,830 | A | 6/1998 | Vacanti et al. |
| 6,607,745 | B2 | 8/2003 | Leneau |
| 7,556,825 | B2 | 7/2009 | Li et al. |
| 7,875,296 | B2 | 1/2011 | Binette |
| 8,039,021 | B2 | 10/2011 | Royer |
| 8,039,258 | B2 | 10/2011 | Harris et al. |
| 8,105,380 | B2 | 1/2012 | Kharazi et al. |
| 8,343,520 | B2 | 1/2013 | Seigneurin et al. |
| 8,349,338 | B2 | 1/2013 | Loginova et al. |
| 8,431,400 | B2 | 4/2013 | Hoffmann et al. |
| 2002/0005205 | A1 | 1/2002 | Barry et al. |
| 2002/0172705 | A1 | 11/2002 | Murphy et al. |
| 2004/0057937 | A1 | 3/2004 | Jahoda et al. |
| 2005/0239897 | A1 | 10/2005 | Pittenger |
| 2006/0088505 | A1 | 4/2006 | Hoffmann |
| 2008/0118478 | A1* | 5/2008 | Kleinsek ............ A61K 38/1808 424/93.7 |
| 2008/0284763 | A1 | 11/2008 | Someya et al. |
| 2009/0130068 | A1 | 5/2009 | Eklund |
| 2009/0142836 | A1 | 6/2009 | Wang et al. |
| 2010/0047305 | A1 | 2/2010 | Naughton et al. |
| 2010/0124573 | A1 | 5/2010 | Naughton et al. |
| 2010/0197019 | A1 | 8/2010 | Toyoshima et al. |
| 2010/0247494 | A1 | 9/2010 | Gregory et al. |
| 2010/0273231 | A1 | 10/2010 | Andreadis |
| 2010/0323027 | A1 | 12/2010 | Lim |
| 2011/0185439 | A1 | 7/2011 | Gaitanaris et al. |
| 2011/0293667 | A1 | 12/2011 | Baksh et al. |
| 2012/0192296 | A1 | 7/2012 | Schneider et al. |
| 2015/0374757 | A1 | 12/2015 | Hoffmann et al. |
| 2016/0136206 | A1 | 5/2016 | Hoffmann et al. |
| 2017/0165299 | A1 | 6/2017 | Hoffmann et al. |
| 2017/0173084 | A1 | 6/2017 | Hoffmann et al. |

FOREIGN PATENT DOCUMENTS

| | | |
|---|---|---|
| EP | 1226234 | 6/2011 |
| WO | 1995001423 | 1/1995 |
| WO | 2003104443 | 12/2003 |
| WO | 2014127047 | 8/2014 |
| WO | 2014205142 | 12/2014 |
| WO | 2015123476 | 8/2015 |
| WO | 2015123477 | 8/2015 |

OTHER PUBLICATIONS

International Search Report and Written Opinion dated Oct. 4, 2014 for Application No. PCT/US2014/016109.
International Search Report and Written Opinion dated Sep. 17, 2014 for Application No. PCT/US2014/043048.
International Search Report and Written Opinion dated May 18, 2015 for Application No. PCT/US2015/015720.
International Search Report and Written Opinion dated May 14, 2015 for Application No. PCT/US2015/015721.
European Supplemental Search Report dated Oct. 11, 2016 for Application No. 14706762.3.
Bajpai, Vivek K. et al., "Clonal multipotency and effect of long-term in vitro expansion on differentiation potential of human hair follicle derived mesenchymal stem cells", Stem Cell Research, 2012, vol. 8, pp. 74-84.
Beckman, Brett, "Potential help for refractory feline chronic gingivostomatitis (proceedings)", dvm360, http://veterinarycalendar.dvm360.com/potential-help-refractory-feline-chronic-gingivo-stomatitis-proceedings, Oct. 1, 2008, pp. 1-3.
Eicheler, Wolfgang et al., "5[alpha]-reductase activity in the human hair follicle conentrates in the dermal papilla", Archives of Dermatological Research, vol. 290, No. 3, Mar. 1, 1998, pp. 126-132.
Gasnereau et al., "Flow cytometry to sort mammalian cells in cytokinesis", Cytometry Part A, 71A, 2007, pp. 1-7.
Hoogduijn et al., "Comparative characterization of hair follicle dermal stem cells and bone marrow mesenchymal stem cells", Stem Cells and Development, 2006, vol. 15, pp. 49-60.
Imai, Ryusuke et al., "Organ culture conditions of human hair follicles", Journal of Dermatological Science, vol. 3, 1992, pp. 163-171.
Jahoda, C A B et al., "Hair follicle dermal cells differentiate into adipogenic and osteogenic lineages", Experimental Dermatology Blackwell Munsgaard, Copenhagen, DK, vol. 12, No. 6, Dec. 1, 2003, pp. 849-859.
Jindo, Toshimasa et al, "The effect of hepatocyte growth factor/scatter factor on human hair follicle growth", Journal of Dermatological Science, vol. 10, 1995, pp. 229-232.
Journal of Dermatological Science, Letter to the Editor, "Connective tissue sheath of hair follicle is a major source of dermal type 1 procollagen in human scalp", vol. 68, 2012, pp. 194-204.
Liu, Jin Yu et al., "Derivation of functional smooth muscle cells from multipotent human hair follicle mesenchymal stem cells", Tissue Engineering Part A, vol. 16, No. 8, Aug. 1, 2010, pp. 2553-3341.
Liu, Jin Yu et al., "Contractile smooth muscle cells derived from hair-follicle stem cells", Cardiovascular Research, vol. 79, 2008, pp. 24-33.
McElwee, Kevin J et al., "Macrophage-Stimulating protein promotes hair growth ex vivo and induces anagen from telogen stage hair follicle in vivo", The Journal of Investigative Dermatology, 2004, vol. 123, pp. 34-40.
McElwee, K J et al., "Cultured peribulber dermal shealth cells can induce hair follicle development and contribute to the dermal shealth and dermal papilla", The Journal of Investigative Dermatology, Nature Publishing Group, GB, vol. 121, Jan. 1, 2003, pp. 1267-1275.
Wu et al., "Enzyme Digestion to Isolate and Culture Human Scalp Dermal Papilla Cells: a More Efficient Method", Arch Dermatol. Res. 297, 2005, pp. 60-67.
Young, R G et al., "Use of mesenchymal stem cells in a collagen matrix for achilles tendon repair", Journal of Orthopaedic Research, vol. 16, No. 4, Jul. 1, 1998, pp. 406-413.

* cited by examiner

COMPOSITIONS AND METHODS FOR TREATING AND REPAIRING TENDONS

CROSS-REFERENCE TO RELATED APPLICATION

This application claims the benefit under 35 U.S.C. § 119(e) of U.S. Provisional Patent Application No. 61/763,908 filed Feb. 12, 2013, which application is incorporated herein by reference in its entirety.

BACKGROUND

Field of the Invention

The present invention relates to compositions and methods for repairing tendons, and more specifically, to compositions comprising non-bulbar dermal sheath cells for use in the treatment and repair of tendons, and for the prevention of tendon injuries.

Description of the Related Art

Tendons are tough bands of fibrous connective tissue that usually connect muscle to bone. Examples of common tendons include the Achilles tendon, which connects the calf muscle to the heel bone, and the Patellar tendon, which connects the patella to the tibia.

Tendons can be injured in a number of ways, including for example, through overuse, strain, disease and general aging. The term "tendinopathy" can be used to refer to a number of injuries, including both those caused by inflammation and micro-tears. Tendons can also be ruptured or torn, typically necessitating surgical intervention.

While there are a number of surgical methods that can be used to treat tendon injuries, even with such methods healing of the tendon can take several years, if they heal at all. The present invention discloses novel compositions and methods for treating tendon injuries, and further provides other related advantages.

SUMMARY

Briefly stated, the present invention provides compositions and methods for treating or preventing tendon injuries utilizing hair follicle derived Non-Bulbar Dermal Sheath ("NDBS") cells. Within one aspect of the present invention methods are provided comprising the steps of (a) preparing vital (i.e., 'living') hair; and (b) culturing the vital hair such that a population of NBDS cells can be obtained. Within preferred embodiments the NBDS cells are isolated.

Within one aspect of the invention methods are provided for isolating NBDS cells, comprising the steps of: (a) preparing vital hair; (b) cleaving the hair prepared in step (a) to remove the hair follicle bulb (which contains the dermal sheath cup and dermal papilla); (c) isolating Non-Bulbar Dermal Sheath tissue; and (d) cultivating the isolated Non-Bulbar Dermal sheath tissue to produce NBDS cells. Within one embodiment of the invention the vital hair is obtained by biopsy from the occipital scalp of a subject. Within another embodiment the hair is cleaved utilizing a micromanipulator and scalpel. Within yet other embodiments, the methods provided herein further comprise the step of conducting enzymatic digestion of the isolated Non-Bulbar Dermal Sheath tissue, optionally, with, for example collagen digesting enzymes such as collagenase, dispase, and leupeptin. Within further embodiments, the cells are passaged over multiple passages.

Within other aspects of the invention, isolated NBDS cells are provided, optionally prepared according to the methods described above, wherein the cells are isolated in order to provide a population which are primarily positive for one or more of: CD 90, CD73 and CD49b, and/or primarily negative for one or more of CD34, CD45 and KRT14 (optionally before or after culturing). Within preferred embodiments the isolated NBDS cells are at least 70%, 80%, 90%, 95%, 98% or 100% positive for one or more of the positive markers described above, and/or at least 80%, 90%, 95%, or 98% negative for one of the negative markers described above. Within preferred embodiments of the invention, isolated NBDS cells have less than 15%, 10%, 5%, or 1% keratinocytes within the cell population and/or less than 15%, 10%, 5%, or 1% melanocytes within the cell population. However, within further embodiments, the isolated NBDS cell population is derived from a population of dermal cells (preferably from a hair follicle) that have some contaminating cell types, including for example, at least 1, 5, 10, 0.0.01%, 0.1%, or 1% keratinocytes in the cell population, and/or at least 5, 10, 0.1%, 0.1% melanocytes. Within further embodiments of the invention the isolated NBDS cells are at least 95% pure, and have at least one contaminating cell type (e.g., at least one keratinocyte) within the cell population.

These NBDS cells (or isolated NBDS cells) may be contained within compositions with other ingredients, such as, for example, serum plasma, fibrin, and/or hyaluronic. Within other embodiments the NBDS cells (or isolated NBDS cells) may be constituted in a composition suitable for injection, e.g., Lactated Ringer's or a buffered saline solution. Other ingredients which may be utilized to form the compositions of the present invention include, for example, components of the extracellular matrix (e.g., glycosaminoglycans (GAGs), heparin sulfate, chondroitin sulfate, keratin sulfate, hyaluronic acid, albumin (e.g., human albumin), elastin, fibronectins and laminins), cytokines and chemokines (e.g., transforming growth factor beta (TGF-beta) and its isoforms, insulin-like growth factor (IGF) and its isoforms, granulocyte-macrophage colony-stimulating factor (GM-CSF), parathyroid-hormone-related protein, hepatocyte growth factor/scatter factor (HGF/SF), macrophage stimulating protein (MSP), epidermal growth factor (EGF), interleukin 6 (IL-6), stromal cell-derived factor 1 (SDF-1), platelet derived growth factor (PDGF) and fibroblast growth factor (FGF) and/or various therapeutic agents (e.g., analgesic agents, anti-inflammatory agents and immunomodulatory agents). Within other embodiments however NBDS cells (and isolated NBDS cells) are provided in compositions that do not have any of the aforementioned ingredients (including for example, serum or plasma).

Within yet other aspects of the invention methods are provided for treating or preventing tendon injuries, comprising the step of administering to a subject a composition comprising NBDS cells are described above (and in preferred embodiments isolated NBDS cells). Within one embodiment, the subject is a mammal selected from the group consisting of humans, horses, pigs, dogs, cats, guinea pigs, rabbits, rats and mice.

Within various embodiments of the invention, the tendon injury is a tendon rupture or tear, or other injury selected from the group consisting of tendinosis, tenosynovitis, and avulsion. Within yet another embodiment, the tendon is an Achilles tendon or the Patellar tendon. Within other embodiments, the tendon is a flexor tendon, or an extensor tendon. Within yet other embodiments tendon injuries should be understood to include a wide variety of tendon associated diseases (including tendinopathies, tendinoses, tendinitis, tenosynovitis, partenonitis, paratenonitis with teninosis, and microtears of a tendon) may also be treated utilizing the compositions provided herein. Representative tendons that may be treated include for example a) the Achilles tendon (e.g., Mid-portion Achilles tendinopathy; Achilles paratendinopathy; Insertional Achilles tendinopathy; Retrocalcaneal bursitis; Superficial calcaneal bursitis: b) Shoulder tendons (e.g., Bicipital tendinopathy; Rotator cuff tendinopathy: c) Elbow tendons (e.g., Medial or Lateral epicondylitis or tennis elbow) d) Hand and Wrist: (e.g., flexor/extensor tendinopathy; flexor/Extensor tenosynovitis; De Quervain's disease; and Dupuytren's contracture; e) hamstring and patellar tendopathies with or without microtears; and f) plantar fasciitis with or without microtears.

The details of one or more embodiments are set forth in the description below. Other features, objects and advantages will be apparent from the description, the drawings, and the claims. In addition, the disclosures of all patents and patent applications referenced herein are incorporated by reference in their entirety.

DETAILED DESCRIPTION OF THE INVENTION

As noted above, the present invention provides hair follicle derived Non-Bulbar Dermal Sheath cells for use in the treatment or prevention of tendon injuries within a mammal. Prior to setting forth the invention however, it may be helpful to an understanding thereof to first set forth definitions of certain terms that are used hereinafter.

Non-Bulbar Dermal Sheath cells, or "NBDS" cells, refers to dermally derived cells (or more specifically, derived from hair follicles). Within preferred embodiments, the sheath cells are obtained from the outer dermal sheath of a hair follicle, above the bulbar portion of the hair root (i.e., above the dermal papilla and dermal sheath cup cells), but below the base of the sebaceous gland canal. NBDS cells may be readily identified by a number of methods, including for example, by the method of preparation and culture (as described below); morphology (see, e.g., FIG. 3); as well as cell specific markers (e.g., NBDS cells are primarily positive for CD 90, CD73 and CD49b, and/or primarily negative for CD34, CD45 and KRT14, either before or after culturing). In all events however, the cells must be of a dermal origin, and more specifically, of a follicular origin.

Expanded Non-Bulbar Dermal Sheath cells, or "eNBDS cells" refers to NBDS cells which have been expanded for several passages in culture, but which retain the ability to produce collagen (e.g., type I collagen) as well as a variety of cytokines and chemokines. As above, unexpectedly, the eNBDS cells can also be immunoregulatory. Within preferred embodiments, the cells can be expanded in culture for 1, 2, 3, 4, 5, 10, 20 or more passages.

"Isolated" NBDS cells refers to a cell population of greater than 70%, 80%, 90%, 95%, 98% or 100% NBDS cells. NBDS cells have the ability to produce collagen (e.g., type I collagen), as well as a variety of cytokines and chemokines. Unexpectedly, the NBDS cells can also be immunoregulatory, making them particularly suitable for treatment of tendon injuries (e.g., by assisting in suppressing any inflammatory response).

Figure 3:
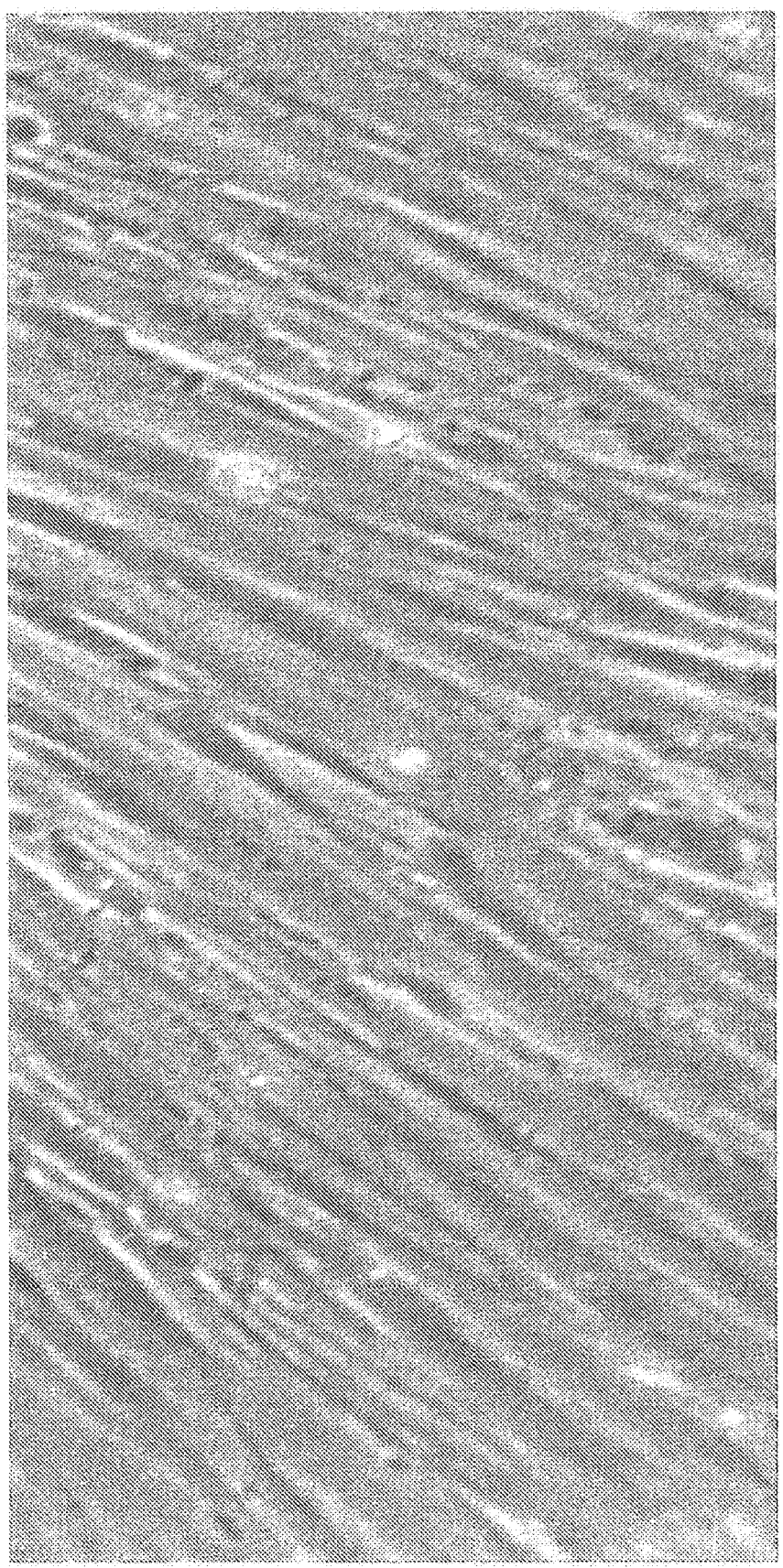
FIG. 3 is a photomicrograph of NBDS cells in culture.

Within certain embodiments of the invention, software or other visualization techniques that can be utilized to visualize cells on a microscopic scale can be used to assess the size, shape, viability and granularity of a large number of cells in a visual field, and ascertain the number of NBDS cells (which are fibroblast-like—as shown in FIG. 3), as opposed to keratinocytes, melanocytes DSCs, and other cell types which are of different morphology). Hence, within one embodiment of the invention methods are provided for isolating NBDS cells comprising the step of culturing cells over at least 1, 2, 3, 4, 5, 6, 10, or 20 passages from a hair follicle such that an isolated population of NBDS cells is produced. Within preferred embodiments the cells placed into dishes or flasks which allow the NBDS cells to adhere, and with each passage non-adherent cells are removed, and the remaining adherent cells released (e.g., by trypsinization), followed by addition of fresh media. Within such embodiments it can be determined when a sufficient population of isolated NBDS cells has been obtained by visualizing the cells in the cell culture in order to assess the number of NBDS cells vs. non-NBDS cells. Visualization techniques include, but are not limited to direct microscopic visualization, staining of the cells for markers (or lack thereof—e.g., for lack of keratin), and light/laser analysis to look at diffraction patterns of the different cell types (see, generally "Laser Scanning Microscopy and Quantitative Image Analysis of Neuronal Tissue" Lidia Bakota and Roland Brandt, eds., Humana Press, 2014; see also "Imaging and Spectroscopic Analysis of Living Cells: Optical and Spectroscopic Techniques", Conn ed., Academic Press, 2012)

Within other embodiments, cell specific markers (e.g., NBDS cells are primarily positive for CD 90, CD73 and CD49b, and/or primarily negative for CD34, CD45 and KRT14 (optionally before or after culturing) can be utilized to assess the degree of NBDS cells vs. contaminant cell types. "Applications of Flow Cytometry in Stem Cell Research and Tissue Regeneration", Krishan, Krishnamurthy, and Totey eds., Wiley-Blackwell, 2010). For example, isolated NBDS cells may be prepared by a) obtaining one or more vital hair follicles; b) releasing cells from the hair follicle (e.g., through the use of enzymes, or by culturing growing cells out of the hair follicle); and c) sorting the cells (e.g., by flow cytometry or through the use of magnetic beads) to obtain a population of isolated NBDS cells. Within certain embodiments of the invention cells in any stage of the process may be optionally cultured as described above (e.g., cells may be cultured for at least 1, 2, 3, 4, 5, 6, 10 or 20 passages as described above, and the resultant cells further isolated by, for example, flow cytometry or magnetic beads.

Within preferred embodiments the isolated NBDS cells are at least 70%, 80%, 90%, 95%, 98% or 100% positive for one or more of the positive markers described above, and/or at least 80%, 90%, 95%, or 98% negative for one of the negative markers described above.

Within preferred embodiments of the invention (and utilizing any of the techniques described herein), isolated NBDS cells have less than 15%, 10%, 5%, or 1% keratinocytes within the cell population and/or less than 15%, 10%, 5%, or 1% melanocytes within the cell population. However, within further embodiments, the isolated NBDS cell population is derived from a population of dermal cells (preferably, from hair follicles) that have some contaminating cell types, including for example, at least 1, 5, 10, 0.0.01%, 0.1%, or 1% keratinocytes in the cell population, and/or at least 5, 10, 0.1%, 0.1% melanocytes.

"Tendon injuries" as utilized herein should be understood to refer to a wide variety of different conditions related to a tendon that result in, or may eventually result in difficulties in adequately utilizing the tendon (and structures associated with the tendon, such as bone and muscle). Tendon injuries can include traumatic injury (e.g., due to a sports injury, overuse, or a medical or surgical intervention), injury of a genetic origin, and disease (which may be caused by any of the above. Representative tendon injuries include, but are not limited to tendinopathies, tendinoses, tendinitis, tenosynovitis, partenonitis, paratenonitis with teninosis, and microtears of a tendon. Representative tendons that may be treated include for example a) the Achilles tendon (e.g., Mid-portion Achilles tendinopathy; Achilles paratendinopathy; Insertional Achilles tendinopathy; Retrocalcaneal bursitis; Superficial calcaneal bursitis: b) Shoulder tendons (e.g., Bicipital tendinopathy; Rotator cuff tendinopathy: c) Elbow tendons (e.g., Medial or Lateral epicondylitis or tennis elbow) d) Hand and Wrist: (e.g., flexor/extensor tendinopathy; flexor/Extensor tenosynovitis; De Quervain's disease; and Dupuytren's contracture; e) hamstring and patellar tendopathies with or without microtears; and f) plantar fasciitis with or without microtears.

Preparation of NBDS

As noted above, the present invention provides methods for isolating NBDS cells. Within one aspect of the present invention such methods comprise the steps of (a) preparing vital hair; and (b) culturing the vital hair such that a population of NBDS cells can be obtained. With respect to step (a), a wide variety of methods may be utilized to obtain vital hair, including for example, surgical methods to remove a variety of hair follicles (along with the skin), or by plucking one or more hair follicles directly from a subject.

Once the vital hair has been obtained, it can be cultured under conditions which allow, and preferentially, promote the growth of NBDS cells. Within preferred embodiments, this culturing under conditions wherein fibroblast-like cells are allowed to proliferate. Within preferred embodiments the step of culturing is performed with serum-free media. After several passages (e.g., at least 2, 3, 4, 5, 10 or more passages), the cultured cells are analysed as described above in order to ascertain whether there is a sufficient quantity of NBDS cells, and whether the cells have been sufficiently isolated from contaminating cells.

Within other aspects of the invention, methods are provided comprising the steps of (a) preparing vital hair; (b) cleaving the hair prepared in step (a) to remove the hair follicle bulb (which contains the dermal sheath cup and dermal papilla); (c) isolating Non-Bulbar Dermal Sheath tissue; and (d) cultivating the isolated Non-Bulbar Dermal sheath tissue to produce NBDS cells.

In order to prepare vital (or 'living') hair, a sample is typically obtained from a given subject (e.g., a mammal such as a human, horses, pig, cat, dog, rabbit, guinea pigs, rats or mice). The sample may be obtained from a variety of sites (e.g., for humans, from the occipital area of the scalp, the chest or thigh, and for horses from the mane or tail). The sample may be obtained via a biopsy, or other suitable means (e.g., by 'plucking', or dissection). Preferably, hair follicles in the anagen phase of development are selected, although other phases of development (e.g., the catagen phase) can also be utilized.

Figure 1D:
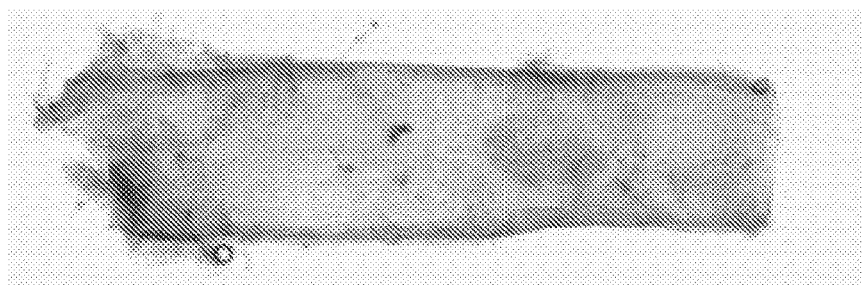
FIG. 1D is the dermal sheath containing NBDS cells (also occasionally referred to as the connective-tissue sheath).
Figure 1C:
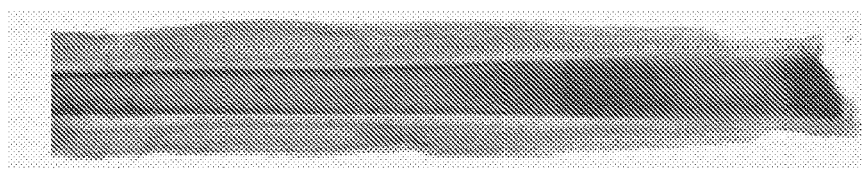
FIG. 1C depicts the hair fiber and associated inner root sheath, and outer root sheath which contain predominantly keratinocytes.
Figure 1B:
FIG. 1 illustrates the dissection of a human hair follicle.
FIG. 1A shows an isolated human hair follicle, which can be cleaved above the bulbar portion of the hair root (i.e., above the dermal papillae and dermal sheath cup cells), but below the base of the sebaceous gland canal, in order to obtain an isolated dermal sheath (see FIG. 1B). The structure depicted in FIG. 1B can be separated into at least two separate components, as shown in FIGS. 1C and 1D.
Figure 1B:
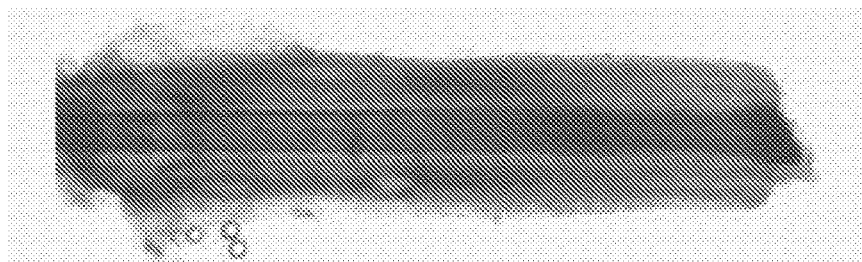
Figure 1A:
Figure 1A:
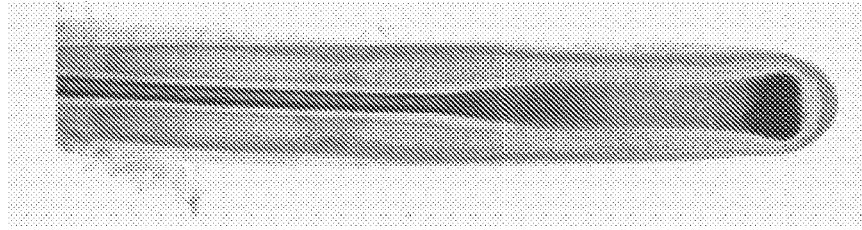
Figure 2:
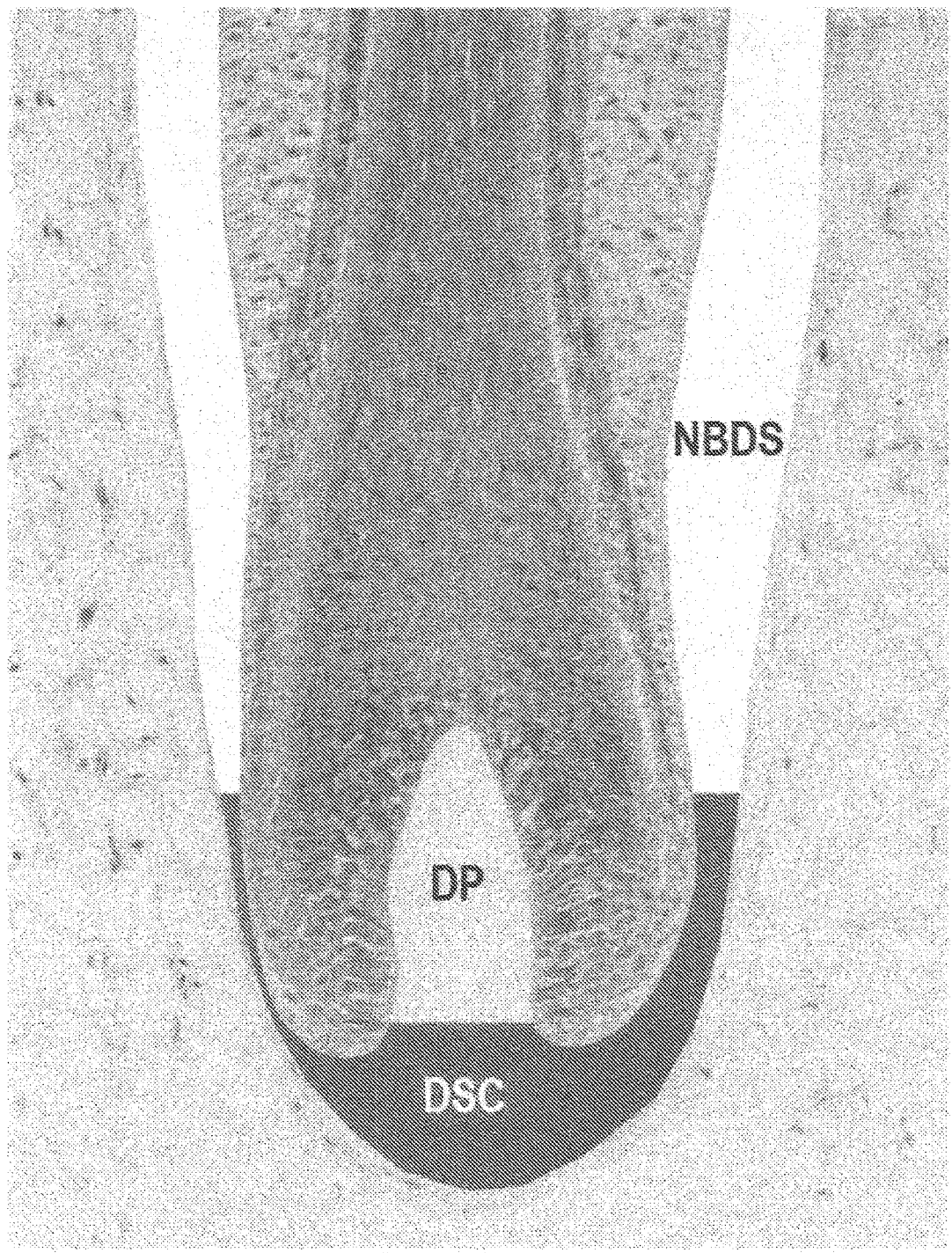
FIG. 2 is an illustration of a hair follicle depicting the origin for dermal papillae ("DP") cells, dermal sheath cup ("DSC") cells, and Non-Bulbar Dermal Sheath ("NBDS") cells.

Once the sample is obtained from the subject, the sample is then separated to isolate the hair follicle, typically utilizing a micromanipulator and scalpel, although other instruments such as needles may also be utilized. Within certain embodiments, the isolated hair follicle as shown in FIG. 1A can be further cleaved above the bulbar portion of the hair root (i.e., above the dermal papillae and dermal sheath cup cells), but below the base of the sebaceous gland canal in order to obtain an isolated dermal sheath (see FIG. 1B). The structure depicted in FIG. 1B can be separated into at least two separate components, as shown in FIGS. 1C and 1D. FIG. 1C depicts the hair fiber and associated inner root sheath, and outer root sheath which contain predominantly keratinocytes, and FIG. 1D is the dermal sheath containing NBDS cells (also occasionally referred to as the connective-tissue sheath).

The dermal sheath (FIG. 1D) can, within certain embodiments, be further separated, for example, by cutting lengthwise along one side, or, by using techniques such as enzymatic digestion (e.g., with collagen digesting enzymes such as collagenase, dispase and leupeptin).

The dermal sheath containing NBDS cells, or the separated NBDS cells can then be cultured in a medium (either with or without serum) which promotes cell proliferation (see e.g., FIG. 3). Suitable media include, for example, DMEM/Hams F12 supplemented with fibroblast growth factor (FGF), fetal calf/bovine serum and antibiotics. Alternatively, cells can be replicated in a serum-free process, in which various combinations of serum-free media and supplements are utilized. The examples of serum-free media include X-Vivo™ and TheraPEAK™ FGM-CD™ containing serum supplements and/or human derived platelet extract. After 3 to 5 days, fresh proliferation medium is typically added to the culture medium. Subsequently the medium can be changed every 2 to 4 days. When the culture has reached approximately 80 to 90% confluence, the cells are detached from the culture flask via trypsinization and seeded in a larger tissue culture flask. This step is repeated for a number of passages (e.g., 2, 4, or 6) until approximately 5 to 100 million cells are obtained.

Once the desired number of cells are obtained, the cells are washed several times, trypsinized, and resuspended in cell transportation medium (CTM), which is composed of ringer lactate, 10% human serum albumin (HAS) and 5% dimethylsulfoxide (DMSO). Cells are counted and adjusted to provide the final concentration of 20 million cells/ml and stored in liquid nitrogen.

Preparation of Compositions Comprising NBDS Cells

As noted above, NBDS cells (and isolated NBDS cells) may be contained within compositions with other ingredients, such as, for example, serum, plasma, platelet-rich-plasma, albumin (e.g., human albumin), fibrin, and/or hyaluronic acid. Other commercially available products may also be utilized to prepare suitable compositions, including for example, TISSEEL and COSEAL (available from Baxter), TISSUCOL, BERIPLAST, QUIXIL, TACHOSIL, and EVICEL. Other polymer-based compositions may also be utilized, including for example, polyethylene glycols, polylactic acids, and poly caprolactones. Within preferred embodiments the composition is provided in one or two parts (e.g., in a double barrelled syringe that admixes components) that is freely flowing and injectable.

Other ingredients may also be included within these compositions, including for example, components of the extracellular matrix (e.g., glycosaminoglycans (GAGs), heparin sulfate, chondroitin sulfate, keratin sulfate, hyaluronic acid, elastin, fibronectins and laminins), cytokines and chemokines (e.g., transforming growth factor beta (TGF-beta) and its isoforms, insulin-like growth factor (IGF) and its isoforms, granulocyte-macrophage colony-stimulating factor (GM-CSF), parathyroid-hormone-related protein, hepatocyte growth factor/scatter factor (HGF/SF), macrophage stimulating protein (MSP), epidermal growth factor (EGF), interleukin 6 (IL-6), stromal cell-derived factor 1 (SDF-1), platelet derived growth factor (PDGF) and fibroblast growth factor (FGF) and/or various therapeutic agents (e.g., analgesic agents, anti-inflammatory agents and immunomodulatory agents).

Methods for Treating Tendon Injuries Utilizing NBDS Cells

Methods are also provided for treating or preventing tendon injuries, comprising the step of administering to a subject a composition comprising NBDS cells (including compositions with isolated NBDS cells as described above). Typically, cells are administered by injection, although within various embodiments, to the extent a surgical method is employed the cells may be provided directly into an open wound. Representative examples of suitable methods of injection include a standard syringe, as well as specialized devices such as those disclosed in U.S. patent application Ser. No. 12/153,248 and PCT Pub. WO/2013/113121, both of which are incorporated by reference in their entirety.

A wide variety of tendon injuries may be treated or prevented utilizing the NBDS cells (and isolated NBDS cells) and methods provided herein. For example, tendon ruptures or tears from accidents or injuries, surgically caused damage or repair can be treated. In addition, other chronic injuries can also be treated, including for example tendinopathies such as tendinitis or tendinosis, tenosynovitis, and avulsion.

A wide variety of tendons can be treated with the NBDS cells (and isolated NBDS cells) and compositions provided herein. For example, within one embodiment tendons are treated that have been injured due to disease and/or trauma (e.g., by medical or surgical trauma or other injury). Tendons may be ruptured, and/or may have complete or partial tears (or microtears). Examples of tendon associated injuries include tendinopathies, tendinoses, tendinitis, tenosynovitis, partenonitis, paratenonitis with teninosis, and microtears of a tendon. Representative tendons that may be treated include for example a) the Achilles tendon (e.g., Mid-portion Achilles tendinopathy; Achilles paratendinopathy; Insertional Achilles tendinopathy; Retrocalcaneal bursitis; Superficial calcaneal bursitis: b) Shoulder tendons (e.g., Bicipital tendinopathy; Rotator cuff tendinopathy: c) Elbow tendons (e.g., Medial or Lateral epicondylitis or tennis elbow) d) Hand and Wrist: (e.g., flexor/extensor tendinopathy; flexor/extensor tenosynovitis; De Quervain's disease; and Dupuytren's contracture; e) hamstring and patellar tendopathies with or without microtears; and f) plantar fasciitis with or without microtears.

A large number of species may be treated with NBDS cells (and isolated NBDS cells) and the compositions provided herein, including for example, mammals such as humans, horses, pigs, dogs, cats, rabbits, guinea pigs, rats and mice.

The following examples illustrate the invention and should not be understood as limiting the scope of the invention.

Example 1

Tissue Sampling

A skin biopsy from the occipital area of the scalp is obtained from a subject as follows. Briefly, once an appropriate area of the scalp has been selected, it is shaved with hair clippers, ensuring some stubble remains. The biopsy area is then thoroughly disinfected and anaesthetized. Once anesthesia has taken effect, a 4-10 mm deep punch biopsy is gently removed from the biopsy site and the incision closed with sutures which can be removed 12-14 days later. The skin biopsy is then packaged under aseptic conditions into a pre-labelled biopsy tube containing biopsy transport medium, composed of DMEM/Hams F12 with antibiotics.

Example 2

Isolation and Cultivation of NBDS Cells

A sterility test is performed on the medium in which the biopsy has been transported to ensure the sample is free from contamination, or alternatively, if the sample is contaminated to ensure that medium with antibiotics is subsequently utilized. The biopsy is then washed several times to remove the biopsy transportation medium and any debris to prepare the tissue for subsequent processing. Hair follicles are processed in Hams F10 by cutting away the skin epithelium with a sterile scalpel and "plucking" or dissecting the whole hair follicle unit from the surrounding dermal tissue using sterile forceps. The hair follicle is gripped with a forceps as close as possible to the skin surface and the follicle exposed by pulling up on the hair in the hair follicle unit. Follicles in the anagen phase (growing phase of the hair cycle, indicated by the visible outer root sheath, and DSC of the hair bulb) are selected for further processing.

NBDS isolation is performed in Hams F10 by first detaching the follicular dermal sheath cup cells and papilla from the rest of the hair follicle using a fine sterile mini-scalpel or needle, and discarded. The dermal sheath containing NBDS cells is removed, and the tissue is prepared for cultivation.

Six to ten dermal sheath tissues are gently placed into 3% hyaluronic acid gel and covered with cell proliferation promoting culture medium such as, for example, DMEM/Hams F12 supplemented with FGF, 10% FCS and antibiotics. After 3 to 5 days, fresh proliferation medium is added to the culture. Subsequently the medium is changed every 2 to 4 days. When the culture has reached approximately 80 to 90% confluence, the cells are detached from the culture flask via trypsinization, and seeded in larger tissue culture flasks. This step is repeated for four passages to obtain approximately 100 million cells.

Once approximately 100 million cells are obtained, the cells are washed with PBS, trypsinized and resuspended in Cell Transportation Medium (CTM: Ringer lactate containing 10% human serum albumin and 5% dimethylsulfoxide). The cells are sedimented by centrifugation and pooled together. The supernatant is aspirated and the cell pellet is resuspended in CTM. Two cell samples/aliquots are removed from the cell-CTM mixture for quality control and cell counting. After the cells are counted, they are sedimented once more by centrifugation, and the resulting pellet is resuspended in CTM to give a final concentration of 20 million cells/ml. The final cell products are stored below −130° C. in liquid nitrogen till shipment.

Example 3

Preparation and Administration of NBDS Cells into a Tendon

Cells are prepared for use in two-chambered syringe. The first chamber contains approximately 20 million cells suspended in 1 ml of total volume. The second chamber contains 1.5 ml of autologous plasma from the patient (prepared separately before this procedure).

The two-chambered syringe is utilized to inject cells (under ultrasound guidance) into multiple locations of the tendon to be repaired.

Example 4

Synthesis of Type I Collagen in Tendon Stretch Studies

Briefly, 1.5 ml of frozen NBDS cells (a total of 3 million cells) are thawed by mixing with 0.15 ml $CaCl_2$ (500 mM stock solution). 1.5 ml of plasma is added and the suspension transferred to an oval casting mold. After approximately one hour a gel will form that can be removed from the mold. The ring is then placed into a machine which can stretch the molded ring structure over time. Measurements may be taken as to the stretch forces that are applied over time.

The molded ring may also be removed, fixed in paraformaldehyde, and immunohistochemcially stained for the presence of one or more proteins (e.g., collagen type I, collagen type III, Biglycan, Tenascin C, Elastin, Tenomoduline and Decorine).

Figure 4B:
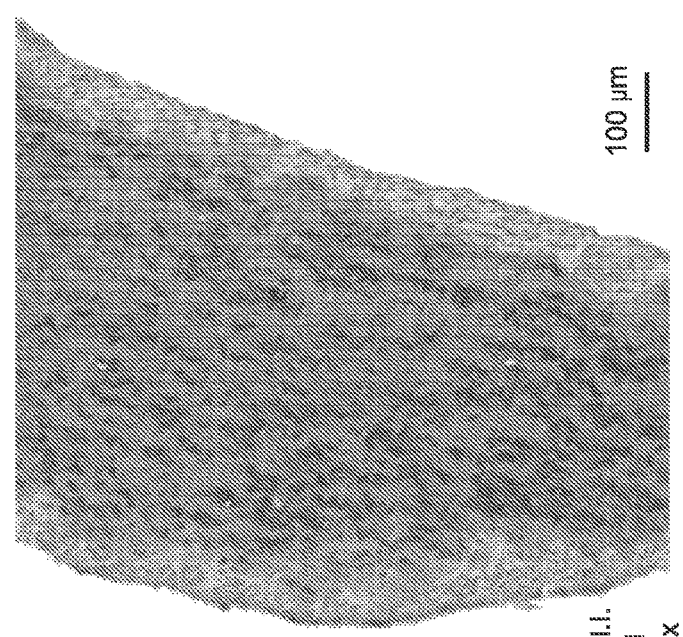
FIG. 4 illustrates NBDS cells which have been stained for collagen production. More specifically, a NBDS/plasma gel mixture was subjected to a mild stretch after 5 days (FIG. 4A) and 12 days (FIG. 4B). The cells in FIG. 4B are noticeably darker than those in FIG. 4A, indicating Type 1 collagen production.
Figure 4A:
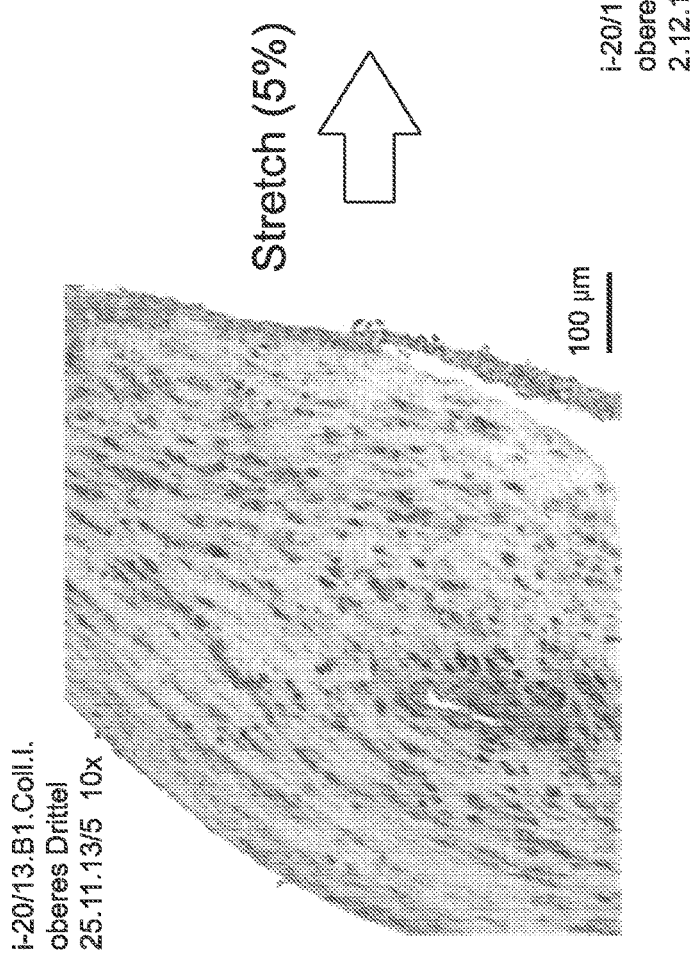

As shown in FIG. 4, the NBDS/plasma gel mixture was subjected to a mild stretch after 5 days (FIG. 4A) and 12 days (FIG. 4B). Samples were immunostained for Type 1 collagen production (with horse-radish peroxidase). FIG. 4B is noticeably darker (brown) than FIG. 4A, indicating that the cells were positive for collagen production, which was increased after mechanical stretching. Results from these studies clearly demonstrate that NBDS cells are able to produce collagen and form tendon-like structures in vitro. In particular, the cells within the molded gel are oriented according to the direction of the stretch (like cells in a normal tendon).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for treating a tendon injury, comprising administering to a subject in need thereof a composition comprising isolated non-bulbar dermal sheath (NBDS) cells; where the isolated NBDS cells were produced by a method comprising
    (a) preparing vital hair;
    (b) cleaving the vital hair prepared in step (a) to remove the hair follicle bulb and obtain an isolated dermal sheath;
    (c) isolating NBDS tissue from the dermal sheath produced in step (b); and
    (d) cultivating the isolated NBDS tissue of step (c) to produce the isolated NBDS cells.

2. The method according to claim 1 wherein said subject is a mammal selected from the group consisting of humans, horses, dogs and cats.

3. The method according to claim 1 wherein said tendon injury is selected from a complete tendon rupture, a partial tendon rupture, and a micro-tear of a tendon.

4. The method according to claim 1 wherein said tendon injury is selected from the group consisting of tendinosis, tenosynovitis, and avulsion.

5. The method according to claim 1 wherein said tendon is the Achilles tendon or the Patellar tendon.

6. The method according to claim 1 wherein said tendon is a flexor tendon.

7. The method according to claim 1 wherein said tendon is an extensor tendon.

8. The method according to claim 1 wherein said vital hair is obtained by biopsy from the occipital scalp of a subject.

9. The method according to claim 1 wherein said vital hair is cleaved utilizing a micromanipulator and scalpel.

10. The method according to claim 1 wherein producing the isolated NBDS cells comprises conducting enzymatic digestion of the isolated Non-Bulbar Dermal Sheath tissue.

11. The method according to claim 10 wherein said enzymatic digestion is conducted with collagenase.

12. The method according to claim 1 wherein said isolated NBDS cells are cultivated over multiple passages in either serum containing or serum-free media.

13. The method according to claim 1 wherein the composition further comprises at least one of serum and plasma.

14. The method according to claim 1 wherein the composition does not contain either serum or plasma.

15. The method according to claim 1 wherein the composition further comprises at least one component selected from the group consisting of fibrin, hyaluronic acid, a component of the extracellular matrix, cytokine, chemokine and therapeutic agent.

16. The method according to claim 15 wherein said component of the extracellular matrix is selected from the group consisting of glycosaminoglycan (GAG), heparin sulfate, chondroitin sulfate, keratin sulfate, hyaluronic acid, elastin, fibronectin and laminin.

17. The method according to claim 15 wherein said therapeutic agent is selected from the group consisting of analgesic agent, anti-inflammatory agent and immunomodulatory agent.

* * * * *